(12) United States Patent
Cox et al.

(10) Patent No.: US 10,013,868 B2
(45) Date of Patent: Jul. 3, 2018

(54) NURSE CALL SYSTEM WITH MOBILE DEVICE INTERFACE

(71) Applicant: Rauland-Borg Corporation, Mount Prospect, IL (US)

(72) Inventors: Carl T. Cox, Mt. Prospect, IL (US); Jennifer A. Holden, Mundelein, IL (US); Michael C. Perkins, Havana, IL (US)

(73) Assignee: Rauldand-Borg Corporation, Mount Prospect, IL (US)

( * ) Notice: Subject to any disclaimer, the term of this patent is extended or adjusted under 35 U.S.C. 154(b) by 0 days.

(21) Appl. No.: 15/010,704

(22) Filed: Jan. 29, 2016

(65) Prior Publication Data
US 2017/0221344 A1    Aug. 3, 2017

(51) Int. Cl.
G08B 5/22      (2006.01)
G08B 25/01    (2006.01)
G08B 25/10    (2006.01)
G06F 19/00    (2018.01)
G16H 40/20    (2018.01)

(52) U.S. Cl.
CPC ....... *G08B 25/016* (2013.01); *G06F 19/3418* (2013.01); *G08B 25/10* (2013.01); *G16H 40/20* (2018.01)

(58) Field of Classification Search
None
See application file for complete search history.

(56) References Cited

U.S. PATENT DOCUMENTS

| 5,838,223 | A | 11/1998 | Gallant et al. |
| 7,679,322 | B1 | 3/2010 | Griffin |
| 8,441,356 | B1 | 5/2013 | Tedesco et al. |
| 9,375,374 | B2 * | 6/2016 | Herman ............... A61G 7/0507 |
| 2006/0049936 | A1 | 3/2006 | Collins et al. |
| 2006/0056616 | A1 | 3/2006 | Heimbrock |
| 2007/0141869 | A1 | 6/2007 | McNeely et al. |
| 2008/0205311 | A1 | 8/2008 | Perkins et al. |
| 2012/0306641 | A1 * | 12/2012 | Howard ............... G08B 25/016 340/539.11 |

(Continued)

FOREIGN PATENT DOCUMENTS

WO    WO 2012/61200 A2    5/2012

OTHER PUBLICATIONS

U.S. Patent and Trademark Office, International Search Report in International Application No. PCT/US2016/016157 (dated Mar. 31, 2016).

(Continued)

*Primary Examiner* — Julie Lieu
(74) *Attorney, Agent, or Firm* — Leydig, Voit & Mayer, Ltd.

(57) ABSTRACT

A nurse call system includes: a host device; and a multifunctional nurse call cable, comprising a nurse call button. The host device includes an interface for the multifunctional nurse call cable. The multifunctional nurse call cable is configured to be connected to the host device and a patient's mobile device, and is further configured to provide power from the host device to the patient's mobile device. The multifunctional nurse call is further configured to initiate a nurse call to a nurse station via the host device in response to the nurse call button being pressed.

21 Claims, 5 Drawing Sheets

(56) References Cited

U.S. PATENT DOCUMENTS

| | | |
|---|---|---|
| 2014/0112321 A1 | 4/2014 | Larson et al. |
| 2015/0257952 A1 | 9/2015 | Zerhusen et al. |
| 2016/0038361 A1* | 2/2016 | Bhimavarapu .......... A61G 7/05 5/600 |
| 2016/0048226 A1* | 2/2016 | Kuciera ................ G08C 19/16 345/173 |
| 2016/0140827 A1* | 5/2016 | Derenne ............. G08B 21/043 340/573.7 |
| 2016/0296143 A1* | 10/2016 | Hayes ................... A61B 5/1115 |

OTHER PUBLICATIONS

U.S. Patent and Trademark Office, Written Opinion in International Application No. PCT/US2016/016157 (dated Mar. 31, 2016).

\* cited by examiner

NURSE CALL SYSTEM WITH MOBILE DEVICE INTERFACE

BACKGROUND

Modern hospitals are generally equipped with nurse call systems, which include various devices located throughout the hospital through which patients and/or nurses are able to communicate over a network (typically an internal hospital network) with one or more centralized nurse stations. One of the components of these nurse call systems is a wall-mounted device located close to a patient bed, which provides various functionality to the patient including, for example, two-way communication hardware that allows for a call to be placed to a nurse station by pushing a button. An accessory remote, designed to be held by the patient, may also be connected to the wall-mounted device and provide similar and/or additional functions (either independently or in combination with the wall-mounted device), including, for example, two-way communication functions as well as remote control over a television in the hospital room.

The accessory remote is sometimes referred to as a "pillow speaker." The Rauland-Borg Responder® line of products includes examples of such pillow speaker devices.

SUMMARY

In an exemplary embodiment, the invention provides a nurse call system. The nurse call system includes: a host device; and a multifunctional nurse call cable, comprising a nurse call button. The host device includes an interface for the multifunctional nurse call cable. The multifunctional nurse call cable is configured to be connected to the host device and a patient's mobile device, and is further configured to provide power from the host device to the patient's mobile device. The multifunctional nurse call is further configured to initiate a nurse call to a nurse station via the host device in response to the nurse call button being pressed.

In another exemplary embodiment, the invention provides a multifunctional nurse call cable. The multifunctional nurse call cable includes: a first interface, configured to connect to a host device; a mechanical nurse call button, configured to generate a nurse call signal for initiating a nurse call via the host device in response to being pressed; and a second interface, configured to connect to a patient's mobile device, wherein the second interface is configured to provide power to the patient's mobile device for charging the patient's mobile device.

In another exemplary embodiment, the invention provides a non-transitory, computer-readable medium having processor-executable instructions stored thereon. The processor-executable instructions, when executed by a processor, facilitate performance of the following: connecting, by a patient's mobile device, to a host device connected to an internal hospital network; initiating, by the patient's mobile device, a nurse call to a nurse station via the internal hospital network; and conducting, by the patient's mobile device, the nurse call.

BRIEF DESCRIPTION OF THE SEVERAL VIEWS OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
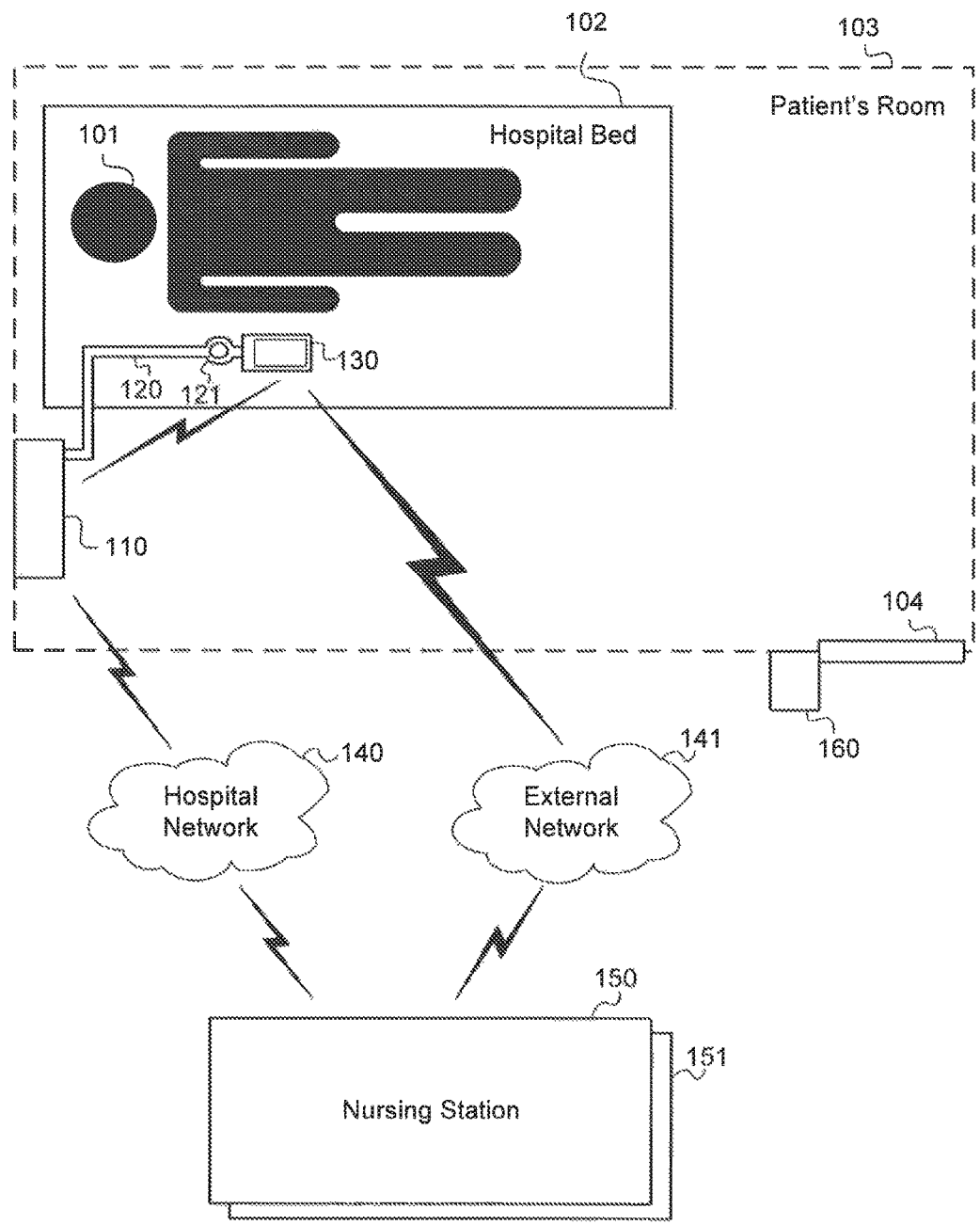
FIG. 1 illustrates an exemplary environment for a nurse call system.

With the proliferation of mobile devices such as smartphones and tablets, patients typically bring a mobile device to the hospital with them and wish to use the device while staying in their hospital room. Particularly for patients that may be staying at a hospital for an extended period, attempting to keep their mobile device charged can be difficult, as outlets are oftentimes not conveniently located near the bed. Further, conventional chargers for mobile devices are not National Fire Protection Association (NFPA) 99-compliant in terms of leakage current, and hospitals may be required to prohibit patients from charging their devices using those conventional chargers while in the hospital.

Exemplary embodiments of the present invention address these issues and achieve various convenience, cost and safety advantages to hospitals and patients by giving the patient the option to replace the conventional pillow speaker accessory device with their mobile device. A mobile app installed on the mobile device allows the patient to perform a variety of operations, including controlling various equipment in the room (e.g., television, HVAC, lighting, curtains/blinds, etc.), reporting and/or receiving data to and/or from hospital staff, speaking with hospital staff for a nurse call, etc. Additionally, a multifunctional nurse call cable with charging capabilities is provided that allows a host device (such as a wall-mounted nurse call host device near the patient's bed) to provide power to the mobile device. The multifunctional nurse call cable may include a mechanical nurse call button, using which the patient can initiate a call to a nurse station (e.g., the patient presses the button, which causes a nurse call signal to be generated and sent to the host device via the interface between the host device and the multifunctional nurse call cable), as well as a charging interface that, for example, can be plugged into the patient's mobile device to provide power to the mobile device battery in an NFPA 99-compliant manner. In a further exemplary embodiment, the multifunctional nurse call cable may further have data communication capabilities and further provide for data communications between the host device and the mobile device.

The host device to which the mobile device is connected via the multifunctional nurse call cable can also provide additional functionality, such as disconnection alerts for both the multifunctional nurse call cable and the mobile device (e.g., a first type of alert for the multifunctional nurse call cable becoming disconnected from the host device and a second type of alert for the mobile device becoming disconnected from the multifunctional nurse call cable). The host device, for example via a short-range wireless connection to the mobile device (such as a Bluetooth pairing), may also be able to identify the patient's device and provide various status updates to computing systems on a local hospital network (such as nurse stations) regarding the mobile device, including, for example, the location of the mobile device, the charging status of the mobile device (e.g., charging versus not charging), the charge level of the mobile device, the existence of the short-range wireless connection with the mobile device (e.g., connected versus not connected), whether the mobile device has downloaded a pillow speaker mobile app, whether the mobile device is dropped (e.g., based on accelerometer data and subsequent comparison of this data to stored limits), etc. The mobile device may also communicate with various hospital computing systems—for example, through an external network such as a guest wireless local area network (WLAN) for the hospital or a cellular network—to report similar status information and/or exchange other information with hospital staff (such as providing the patient with diagnostic or treatment information and/or having the patient answer questionnaires), as well as provide various other functionality to the user such as controlling components of the room (such as television, HVAC, lighting, window blinds/curtains systems) via, for example, a browser app accessing a hospital website or a pillow speaker app. In a further exemplary embodiment, the multifunctional nurse call cable may further provide a data connection to the hospital's wired LAN for purposes similar to, or in conjunction with, those outlined above.

By using these exemplary embodiments of the present invention, patients and hospitals are able to mitigate the risk of hospital-spread disease by avoiding the need for patients to use the same pillow speaker one after another. Further, patients are able to have a more convenient experience at the hospital by being able to charge their mobile devices at their hospital beds, and being able to use an app on their mobile device to perform various operations instead of having to use a hospital-provided pillow speaker device. This also saves costs for the hospital, which is no longer to maintain as many pillow speakers in stock, and provides the hospital with a platform through which they can more flexibly communicate with the patient. It will be appreciated that the foregoing discussion of advantages is merely exemplary, and that other advantages not expressly discussed here are also achieved and contemplated.

FIG. 1 illustrates an exemplary environment for a nurse call system usable with exemplary embodiments of the claimed invention, FIG. 1 depicts a patient 101 in a hospital bed 102 in the patient's room 103. A wall-mounted host device 110 provides NFPA-99 compliant charging, via multifunction cable 120, to the patient's mobile device 130 at a location easily accessible to the patient 101 while in bed 102. The multifunctional nurse call cable 120 includes a mechanical button 121 for allowing the patient 101 to initiate a nurse call to a nurse station 150 via the wall-mounted host device 110 (and/or the mobile device 130). Additionally, the mobile device 130 includes a mobile app that also allows the patient 101 to initiate a nurse call via the mobile device 130 (and/or via the host device 110). The nurse call system further includes, for example, a corridor light 160 outside the door 104 of the patient's room 103, which is configured to light up with lights of different colors or use other visual indicators (such as blinking lights) to provide various visual notifications to hospital staff passing by, for example, to indicate that the patient 101 is need of attention.

The patient 101 is also able to connect the mobile device 130 to the host device 110 to exchange data via, for example, a short-range wireless connection such as a Bluetooth pairing. Using a short-range wireless pairing, the host device 110 is thus able to identify the paired mobile device 130 as being associated with a particular patient, and is able to report status information to hospital staff over the hospital network 140 specifically relating to that patient (for example, the location of the mobile device 130 as being in the patient's room 103, various status information relating to the mobile device 130 relating to battery charge, whether or not the mobile app is downloaded, whether the mobile device 130 is dropped, etc.).

The patient is also able to operate the mobile device 130, for example, via a pillow speaker app installed on the mobile device 130, to accomplish various operations by communicating with a hospital systems such as a nurse station 150 or other hospital systems 151. The mobile device 130 is able to communicate with the appropriate system over the external network 141 and/or via the hospital network 140.

For example, the patient 101 may control various systems in the room (e.g., television, HVAC, lighting, curtains/blinds, etc.) by inputting commands into the mobile device 130. The mobile device 130 then communicates with the appropriate system accordingly. In one specific example, for a system connected to an external network 141 (i.e., a network other than the hospital's private local wireless network) such as a television connected to a guest WLAN network, the mobile device 130 may communicate with the system directly over the external network 141.

In another example, the patient 101 interacts with a system connected only to the local hospital network 140 (such as placing a nurse call to the nurse station 150 through the hospital's nurse call system). In this example, the mobile device 130 may communicate with the nurse station 150 through its short-range wireless connection to the host device 110, which is connected to the nurse station 150 over the local hospital network 140. In a further exemplary embodiment, the mobile device 130 may communicate with the nurse station (and the local hospital network) via a data connection through the multifunctional nurse call cable.

It will be appreciated that the configurations discussed above with respect FIG. 1 are only exemplary, and that other configurations of nurse call environments for exemplary embodiments of the present invention are also contemplated. For example, in another exemplary environment, multiple hospital beds 102 and multifunctional nurse call cables 120 are associated with a single wall-mounted host device 110 for a multiple-patient hospital room. In other exemplary environments, it will be appreciated that the host device 110 and the mobile device 130 may both communicate with the hospital computing systems via the hospital network 140 and/or via the external network 141. In another exemplary environment, instead of the mobile device 130 utilizing a specific pillow speaker mobile app to carry out the various operations discussed above, the mobile device 130 may utilize a conventional browser app that accesses a website providing similar functionality (e.g., the patient 101 can interact with the website to place nurse calls, exchange information with hospital staff, and/or control various systems in the hospital room).

In yet another exemplary environment, additional host devices 110 (with corresponding cables) may be provided in visiting areas (e.g., in the same room or in an adjoining room) for visitors of the patient 101, such as family members, to use on behalf of the patient 101 (for example, a family member could place a nurse call, adjust room settings, communicate with hospital staff, etc., on behalf of the patient 101). Distinguishing between requests or commands input by family members versus requests or commands input by a patient may be based on an identification of which host device the request or command originates from and/or an identification of a paired mobile device from which the request or command originates.

In another exemplary environment, the system may further include a dock or mobile device holder upon which the mobile device 130 may be placed or inserted (in a usable position) while connected to the multifunctional nurse call cable 120.

It will also be appreciated by those of skill in the art that the execution of the various device-implemented processes and steps described herein may occur via the computerized execution of processor-executable instructions stored on a non-transitory computer-readable medium, e.g., RAM, ROM, PROM, Flash, volatile, nonvolatile, or other electronic memory mechanism. Thus, for example, the operations performed by computing devices (such as the mobile device 130, host device 110, and hospital computing systems) discussed herein may be carried out according to stored instructions and/or applications installed thereon.

Figure 2:
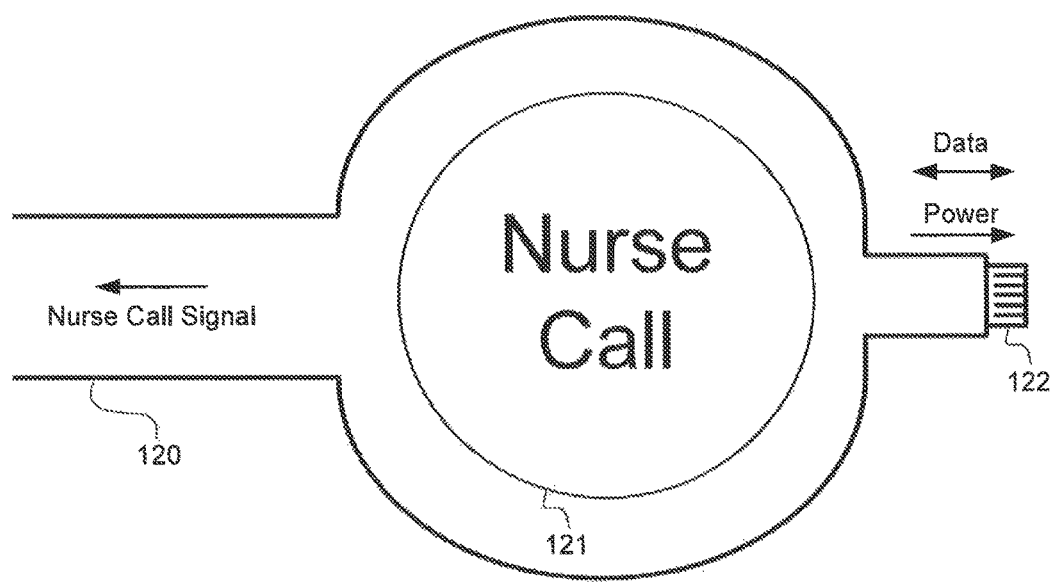
FIG. 2 illustrates an exemplary multifunctional nurse call cable.

FIG. 2 illustrates an exemplary multifunctional nurse call cable 120 according to an exemplary embodiment. The multifunctional nurse call cable 120 includes a mechanical button 121, which provides a nurse call signal to a connected host device 110 to cause the host device 110 to initiate a nurse call, for example, over the hospital network 140 to a nurse station 150. The multifunctional nurse call cable 120 also includes a mobile device interface 122, which may be connected to a mobile device 130 to provide power to the mobile device 130 in a NFPA 99-compliant manner and/or to provide for data communications between the mobile device 130 and the host device 110. In one example, the multifunctional nurse call cable 120 interfaces with the host device 110 and the mobile device 130 via one or more types of Universal Serial Bus (USB) connections. In other examples, other types of wired interfaces for the multifunctional nurse call cable 120 to interface with the host device 110 and the mobile device 130 are used, such as other serial communications protocols.

In another exemplary embodiment, the single mechanical button 121 may be replaced with multiple mechanical buttons for different nurse call-related functions (for example, separate buttons to press for different patient requests), and that each of the multiple mechanical buttons corresponds to the host device 110 making a different type of nurse call.

In another exemplary embodiment, multiple charging interfaces 122 of different types may be provided at the end of the multifunctional nurse call cable 120 to be able to accommodate different types of mobile devices 130.

In another exemplary embodiment, the multifunctional nurse call cable 120 may include microphone and/or speaker hardware to allow audio communication and entertainment audio via the multifunctional nurse call cable 120 (as an alternative to audio communication and entertainment audio via the host device 110, which may be located farther from the patient 101, and as an alternative to audio communication and entertainment audio via the mobile device 130, which may not necessarily be connected or in use). The microphone and/or speaker hardware may be positioned near the mechanical button 121 to ensure that it is proximate to the patient 101.

In certain exemplary embodiments, the multifunctional nurse call cable 120 may be reused, including sterilization of the multifunctional nurse call cable 120 before use by a new patient. In other exemplary embodiments, the multifunctional nurse call cable 120 may be disposed of after use by a patient. In further other exemplary embodiments, the multifunctional nurse call cable 120 may be taken home by the patient after discharge from the hospital for the patient to use as a charging cable.

Figure 3A:
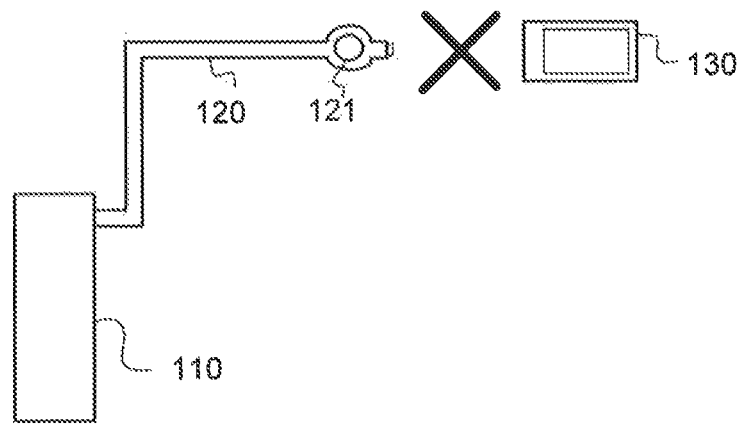
FIG. 3A illustrates an exemplary situation where the mobile device is disconnected from a multifunctional nurse call cable while the multifunction cable is connected to a host device.

FIG. 3A depicts an exemplary situation where the mobile device 130 is disconnected from the multifunctional nurse call cable 120 while the multifunctional nurse call cable 120 is connected to the host device 110. In this situation, the host device 110 may notify hospital staff, e.g., via a warning provided to the nurse station 150, that the mobile phone 130 is disconnected. This may prompt a hospital staff member to visit the patient's room 103 to check on the patient 101, e.g., to make sure the patient 101 is still in the room 103 or to check if they need help with plugging the phone back in 130. In an exemplary implementation, this notification or warning may be a relatively lower priority notification or warning, given that the patient 101 is still able to call the nurse station 150 via the mechanical button 121 on the multifunctional nurse call cable 120.

Figure 3B:
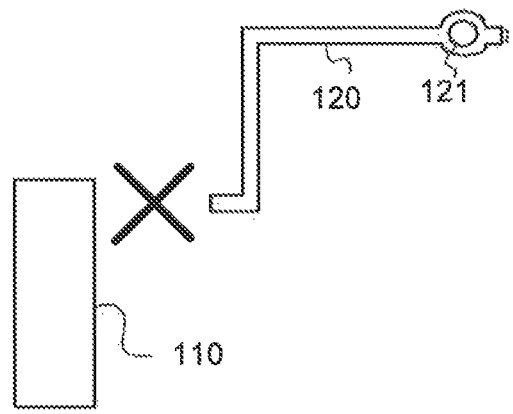
FIG. 3B illustrates an exemplary situation where a multifunctional nurse call cable is disconnected from a host device.

FIG. 3B depicts an exemplary situation where the multifunctional nurse call cable 120 is disconnected from the host device 110. In this situation, the host device 110 may provide a relatively higher priority notification or warning to hospital staff for someone to come check on the patient 101 immediately, as the patient 101 might not be able to contact hospital staff at all for nurse calls while the multifunctional nurse call cable 120 is disconnected from the host device 110.

In this manner, the host device 110 is able to provide different responses with respect to disconnections at either end of the multifunctional nurse call cable 120. A relatively lower priority notification (for example, via a relatively lower priority indication on a corridor light 160 and a relatively lower priority message sent to and displayed at the nurse station) is issued by the host device in response to detecting disconnection at the mobile device end of the multifunctional nurse call cable 120. A higher priority notification (for example, via a relatively higher priority indication on a corridor light 160 and a relatively higher priority message sent to and displayed at the nurse station) is issued by the host device in response to detecting disconnection at the host device end of the multifunctional nurse call cable 120, or, alternatively, an automatic nurse call is placed by the host device 110 in response to detecting disconnection at the host device end of the multifunctional nurse call cable 120 (e.g., to make sure hospital staff goes an reconnects the multifunctional nurse call cable 120 immediately).

The host device 110, as well as other nurse call system components (such as the corridor light 160 or other notification devices), may also generate an audio and/or visual alert upon detecting disconnection of the mobile device 130 from the multifunctional nurse call cable 120 or disconnection of the multifunctional nurse call cable 120 from the host device 110, for example, to notify the patient 101 and/or others in the room that the disconnection has occurred.

In another exemplary embodiment, a warning or notification may also be generated by the host device 110 in the event that the host device 110 loses its short-range wireless connection pairing with the mobile device 130. In one example, a relatively lower priority notification is provided if the host device 110 determines that the mobile device 130 is still docked and charging when the wireless connection is lost (indicating that the mobile device 130 is still likely in the room), while a relatively higher priority notification is provided or an automatic nurse call is placed when the mobile device 130 is not docked when the wireless connection is lost (indicating that the patient 101 might have taken the mobile device 130 and left the patient's room 103).

The host device 110 is able to detect the disconnection of the mobile device 130 from the multifunctional nurse call cable 120 through a variety of techniques. For example, the host device 110 can determine whether there is a load drawing current from the host device 110 from its interface with the multifunctional nurse call cable 120 that is consistent with a mobile device 130 being connected at the end of the multifunctional nurse call cable 120. In another example, the mobile device 130 reports to the host device 110, via the short-range wireless communication link between them, that the mobile device 130 is no longer plugged into a charging interface and receiving charge.

In an exemplary embodiment, the host device is able to detect the disconnection also by using a supervised data connection (such as a periodically-polled watchdog data stream). Further, there may additionally be an active detection component in the "dongle" (where the button is located); this active detection component is able to assist the host device in differentiating between the cable being disconnected from the host and the cable being disconnected from the mobile device. In an exemplary implementation, the active detection component includes a microprocessor in the dangle that is in communication with both the mobile device and the host device. The active detection component is particularly suitable in cases where the process of sensing the charging current to determine connectivity is unreliable, such as in cases when the charging current goes to zero even with the mobile device plugged in (e.g., due to charging characteristics purposely built into the mobile device by the manufacturer).

In other exemplary embodiments, the host device 110 is also able to detect the disconnection of the multifunctional nurse call cable 120 from the host device 110 through a variety of techniques. For example, the multifunctional nurse call cable 120 can be configured to draw a small leakage current from the host device 110 such that, if no current is detected as being drawn from the interface for the multifunctional nurse call cable 120, the host device 120 determines that the multifunctional nurse call cable 120 is disconnected. In another example, the host device 110 relies on a passive electrical network (i.e. a resistor) between the multifunctional nurse call cable 120 and the host device 110 as an open/closed switch to determine whether the multifunctional nurse call cable 120 is connected. The active detection component may also be useful in this case where it is desirable to have data-supervised connections rather than a passive electrical network.

Figure 4:
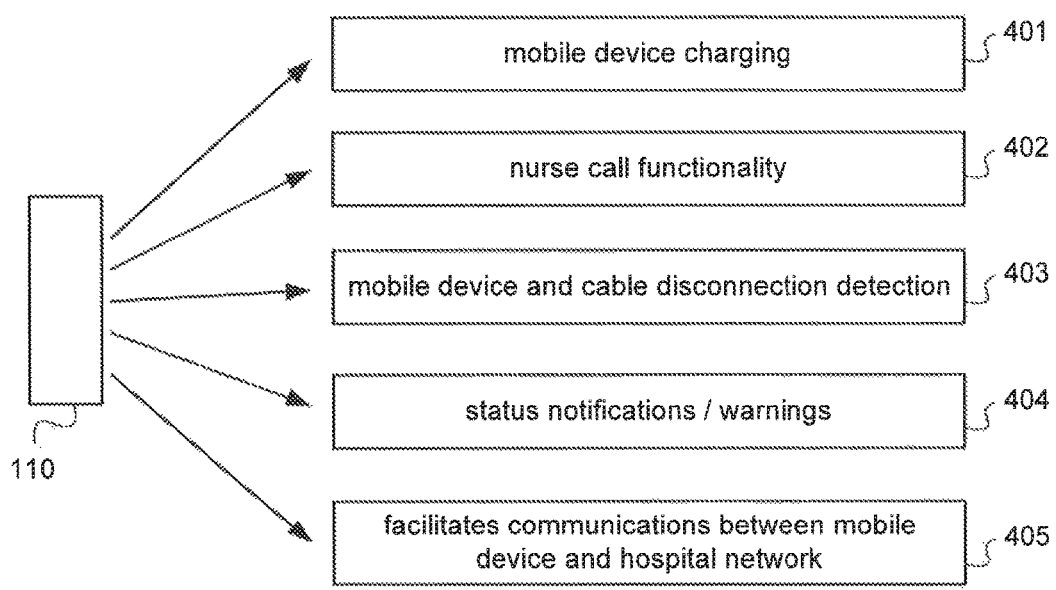
FIG. 4 illustrates exemplary functionality provided by a host device.

FIG. 4 illustrates exemplary functionality provided by the host device 110. Element 401 corresponds to charging the patient's mobile device 130. As discussed above, via the multifunctional nurse call cable 120, the host device 110 provides power to the patient's mobile device 130 in a convenient and NFPA-compliant manner, such that the patient 101 is able to dock and/or charge his or her mobile device 130 at the hospital bed 102 or proximate to the hospital bed 102.

Element 402 corresponds to nurse call functionality. Microphone and/or speaker hardware in the host device 110 allows two-way nurse calls to be conducted using the host device 120. Such calls may be triggered, for example, by pressing a mechanical nurse call button on the host device 110 itself, by pressing a mechanical nurse call button 121 on the multifunctional nurse call cable 120, by using an input interface on the mobile device 130, and/or detection of certain conditions (such as the multifunctional nurse call cable 120 becoming disconnected; the short-range wireless pairing between the mobile device 130 and the host device 110 being lost; or the mobile device 130 being dropped).

Element 403 corresponds to detection of disconnection of the mobile device 130 and/or disconnection of the multifunctional nurse call cable 120, as discussed above with respect to FIGS. 3A-3B. The host device 110 may itself generate different types of audio or visual notifications in response to detecting such disconnections, and/or interact with other hospital systems via the hospital network 140 (such as nurse station 150 or corridor light 160) to generate appropriate notifications or warnings.

In an exemplary embodiment, there may be a programmable delay time (e.g. 10 minutes) to allow a delay between disconnecting the phone from the multifunctional nurse call cable and the generation of a disconnect alarm. There may also be an override button on the dongle that may be pressed prior to disconnection to prevent a disconnect alarm. In another alternative implementation, the user may press an override button on the mobile app to prevent the disconnect alarm from occurring.

Element 404 corresponds to providing various status notifications or warnings relating to the patient 101 and/or the mobile device 130 to hospital systems via the hospital network. For example, the host device 110, based on a short-range wireless pairing with the patient's mobile device 130, can indicate to hospital staff that the mobile device 130 is still in the vicinity of the host device 110 based on the existence of the short-range wireless link, indicating that the patient 101 is still likely in the patient's room 103. Further, a unique patient ID corresponding to the patient 101 may be associated with the mobile device 130 (e.g., in the mobile device memory or in the host device memory), and a particular room ID may be associated with the host device 110, such that the host device 110 may report which room a particular patient's paired mobile device 130 is in.

The host device 110 may further report other information obtained via the short-range wireless link regarding the mobile device 130 to hospital staff to allow hospital staff to respond accordingly. For example, the host device 110 may report: whether or not the mobile device 130 is charging or not; the charge level of the mobile device battery; and/or whether the mobile device 130 has a pillow speaker app installed thereon or not. The host device 110 may also report, for example, whether a mobile device 130 connected to the host device 110 via the multifunctional nurse call cable 120 is paired to the host device 110 or not. The host device 110 may also respond to the mobile device 130 being dropped by automatically sending a notification or warning to hospital staff via the hospital network and/or initiating a nurse call (as discussed above with respect to element 402).

Element 405 corresponds to the host device 110 facilitating communications between the mobile device 130 and systems on the hospital network 140. For example, for a nurse call performed using the mobile device's audio input and playback hardware, the audio data may be communicated to the host device 110 via the short-range wireless connection between the mobile device 130 and the host device 110, and the host device 110 relays the audio data for the nurse call over the hospital network 140 to the nurse station 150. In another example, when the patient 101 uses the mobile device 130 to input commands relating to hospital systems connected to the hospital network 140 (such as HVAC, lighting, blind/curtain controls in the event that such systems are connected to the hospital network 140 rather than to an external network 141), the host device 110 relays those commands over the hospital network 140 to the appropriate hospital systems. In another example, the patient 101 and hospital staff use the mobile device 130 to communicate various data with each other via the hospital network 140 and the short-range wireless connection between the mobile device 130 and the host device 110 (such as nurses/doctors pushing messages to the patient 101 or the patient 101 pushing messages to the nurses/doctors; pushing educational information to the patient 101, e.g., relating to treatment; providing the patient 101 with satisfaction surveys or other questionnaires; etc.).

Figure 5:
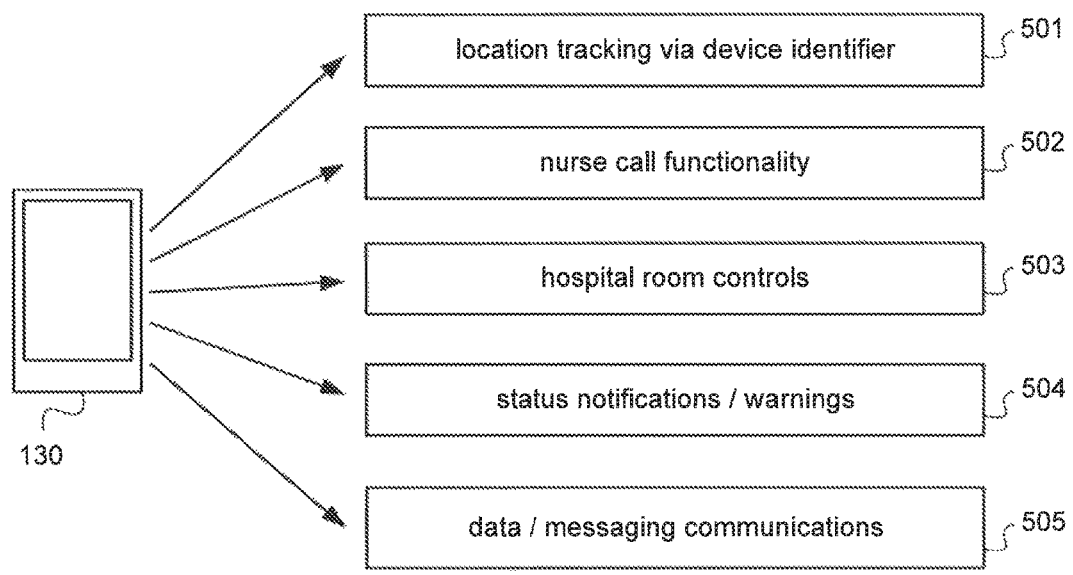
FIG. 5 illustrates exemplary functionality provided by a mobile device.

FIG. 5 illustrates exemplary functionality provided by the mobile device 130. This functionality may be provided, for example, when a pillow speaker app is installed on the patient's mobile device 130. In another exemplary implementation, the patient's mobile device 130 may be able to provide this functionality via a browser app that is accessing a website that provides an interface for these operations.

Element 501 corresponds to the mobile device 130 being used to keep track of the patient's location. For example, when the mobile device 130 is paired with the host device 110 in the patient's room 103, the mobile device 130 may report, via an external network 141 (or via the hospital network 140 via its short-range wireless connection to the host device 110), that the mobile device 130 is still in the vicinity of the host device 110 and still in the patient's room 130. When the patient 101 leaves the room, for example, being transferred to another department of the hospital for an operation, the patient 101 may take the mobile device 130 along with, and the mobile device 130, based on pairings to hospital devices in other locations (or based on connections to wireless access points in other areas of the hospital), is able to provide updates as to the mobile device's (and thus the patient's) location. Alternatively, the patient 101 may also input his or her location into the mobile device 130 to inform hospital staff of his or her location.

Element 502 corresponds to the mobile device 130 providing nurse call functionality. For example, through a pillow speaker app or through a browser app, the patient 101 may press a nurse call button on the mobile device 130 (e.g., presented via a touch screen of the mobile device) to initiate a nurse call. As discussed previously herein, the nurse call may be conducted using audio input and playback hardware of the mobile device 130, of the multifunctional nurse call cable 120, or of the host device 110. Further, if the patient 101 is not in the patient's room 103, the location tracking fi discussed above with respect to element 501 may be used to locate the patient 101 based on where the nurse call placed by the mobile device 130 (e.g., via a short-range wireless connection, a wireless access point, or a cellular network) is originating from. This is advantageous, for example, to remedy situations where a patient might be transported to some other area of the hospital and inadvertently left there by hospital staff.

Element 503 corresponds to the mobile device 130 providing the patient 101 with control over various systems corresponding to the patient's room 103. For example, the mobile device 130 may provide various remote control interfaces for controlling a television in the room (e.g., channel controls, volume controls, menu controls, etc.), adjusting HVAC settings for the room (e.g., raising/lowering the temperature), opening or closing curtains or blinds in the room, making the lights in the room brighter or dimmer or shutting them on or off, etc. Such control commands may be provided to the respective systems by the mobile device 130 via an external network 141 such as a guest WLAN, or via the hospital network 140 through the mobile device's connection to the host device 110.

Element 504 corresponds to providing various status notifications or warnings to hospital systems. In addition to location tracking as discussed above with respect to element 501, other status information that the mobile device 130 may report includes, for example: whether or not the mobile device 130 is charging or not; the charge level of the mobile device battery; and/or whether the mobile device 130 has a pillow speaker app installed thereon or not. The mobile device 130 may also report, for example, whether the mobile device 130 is paired to the host device 110 or not. The mobile device 130 may also respond to detecting that the mobile device 130 has been dropped by automatically sending a notification or warning to hospital staff via the hospital network and/or initiating a nurse call (e.g., via the mobile device 130 itself or via the host device 110). Such status notifications or warnings may be provided by the mobile device 130 via an external network 141 such as a guest WLAN, or via the hospital network 140 through the mobile device's connection to the host device 110.

Element 505 corresponds to the mobile device 130 providing an interface for the patient 101 to use in various data or messaging communications with hospital staff. For example, nurses/doctors may push messages to the patient 101, which are displayed at the mobile device 130, or the patient 101 may send messages to the nurses/doctors using a messaging interface of the mobile device 130. This messaging may be implemented by SMS, MMS, TCP/IP, or other standard protocols, or it may be a unique and specially-designed protocol. A specially-designed protocol could include supervised message exchanges that would allow for multiple attempts at message delivery and provide alerts when messages are not received after a given number of tries and number of delivery attempts. Additionally, educational information may be pushed to the patient 101 and displayed on the mobile device 130 (e.g., relating to treatment). Satisfactions surveys and other questionnaires may also be presented to the patient 101 on the mobile device 130, and the patient uses the mobile device 130 to respond and transmit the responses back to the hospital computing systems. Such data and messaging communications may be exchanged between the mobile device 130 and the hospital computing systems via an external network 141 such as a guest WLAN, or via the hospital network 140 through the mobile device's connection to the host device 110. The mobile device 130 may also be used for follow-up communications with a patient even after the patient has left the hospital, e.g., via the mobile device's connection to an external cellular network or the Internet (with a patient ID being linked to the mobile device 130 for identifying the correct mobile device 130 to which these follow-up communications are provided).

It will be appreciated that the functionality discussed above with respect to the host device 110 and the mobile device 130 and FIGS. 4 and 5 is merely exemplary, and that other operations, including different types of information or notifications/warnings, are also contemplated.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A nurse call system comprising:
   a host device; and
   a multifunctional nurse call cable, comprising a nurse call button;
   wherein the host device comprises an interface for the multifunctional nurse call cable;
   wherein the multifunctional nurse call cable is configured to be connected to the host device and a patient's mobile device, and is further configured to provide power from the host device to the patient's mobile device; and
   wherein the multifunctional nurse call cable is further configured to initiate a nurse call to a nurse station via the host device in response to the nurse call button being pressed.

2. The nurse call system according to claim 1, wherein the power provided from the host device to the patient's mobile device via the multifunctional nurse call cable is National Fire Protection Association (NFPA) 99 compliant.

3. The nurse call system according to claim 1, wherein the multifunctional nurse call cable is further configured to provide data communications between the host device and the patient's mobile device.

4. The nurse call system according to claim 1, wherein the host device is configured to detect disconnection of the patient's mobile device from the multifunctional nurse call cable while the multifunctional nurse call cable is connected to the host device, and in response to detecting the disconnection, transmit a notification to the nurse station.

5. The nurse call system according to claim 1, wherein the host device is configured to detect disconnection of the multifunctional nurse call cable from the host device, and in response to detecting the disconnection, transmit a notification to the nurse station.

6. The nurse call system according to claim 1, wherein the host device is configured to detect disconnection of the patient's mobile device from the multifunctional nurse call cable while the multifunctional nurse call cable is connected to the host device, and to detect disconnection of the multifunctional nurse call cable from the host device; and
   wherein the host device is further configured to transmit a first type of notification to the nurse station in response to detecting disconnection of the patient's mobile device from the multifunctional nurse call cable while the multifunctional nurse call cable is connected to the host device, and to transmit a second type of notification to the nurse station in response to detecting disconnection of the multifunctional nurse call cable from the host device.

7. The nurse call system according to claim 1, wherein the host device is configured to communicate with the patient's mobile device via a short-range wireless protocol.

8. The nurse call system according to claim 7, wherein the patient's mobile device is further configured to be paired to the host device via the short-range wireless protocol.

9. The nurse call system according to claim 1, wherein the host device is a wall-mounted computing device located in a hospital room.

10. The nurse call system according to claim 1, wherein the host device is configured to provide a communications interface through which the patient's mobile device communicates with an internal hospital network.

11. A multifunctional nurse call cable, comprising:
    a first interface, configured to connect the multifunctional nurse call cable to a host device;
    a mechanical nurse call button, configured to generate a nurse call signal for initiating a nurse call via the multifunctional nurse call cable and the host device in response to being pressed; and
    a second interface, configured to connect the multifunctional nurse call cable to a patient's mobile device, wherein the second interface is configured to provide power to the patient's mobile device for charging the patient's mobile device.

12. The multifunctional nurse call cable according to claim 11, wherein the power provided to the patient's mobile device through the multifunctional nurse call cable is National Fire Protection Association (NFPA) 99 compliant.

13. The multifunctional nurse call cable according to claim 11, wherein the first interface and/or the second interface are interfaces configured for a serial communications protocol.

14. The multifunctional nurse call cable according to claim 11, wherein the second interface is further configured to provide data from the host device to the patient's mobile device and the first interface is further configured to provide data from the patient's mobile device to the host device.

15. A non-transitory, computer-readable medium having processor-executable instructions stored thereon, the processor-executable instructions, when executed by a processor, facilitating performance of the following:

connecting, by a patient's mobile device, via a multifunctional nurse call cable, to a host device connected to an internal hospital network, wherein the multifunctional nurse call cable comprises a mechanical nurse call button configured to generate a nurse call signal for initiating a nurse call via the multifunctional nurse call cable and the host device in response to being pressed;

initiating, by the patient's mobile device, a nurse call to a nurse station via the multifunctional nurse call cable, the host device, and the internal hospital network; and conducting, by the patient's mobile device, the nurse call via the multifunctional nurse call cable, the host device, and the internal hospital network.

16. The non-transitory, computer-readable medium according to claim 15, wherein connecting to the host device comprises pairing the patient's mobile device to the host device via a short-range wireless protocol.

17. The non-transitory, computer-readable medium according to claim 15, wherein the processor-executable instructions, when executed, further facilitate performance of the following:

receiving, by the patient's mobile device, a user command; and communicating, by the patient's mobile device, the user command to a corresponding control system.

18. The non-transitory, computer-readable medium according to claim 17, wherein the user command is communicated to the corresponding control system via the host device and the internal hospital network.

19. The non-transitory, computer-readable medium according to claim 17, wherein the corresponding control system is one of the group consisting of: an entertainment system, a lighting system, and a heating ventilating and air conditioning (HVAC) system.

20. The non-transitory, computer-readable medium according to claim 15, wherein the processor-executable instructions, when executed, further facilitate performance of the following:

detecting, by the patient's mobile device, that the patient's mobile device is dropped; and transmitting, by the patient's mobile device, in response to detecting the patient's mobile device being dropped, a communication to a nurse station via the host device and the internal hospital network.

21. The non-transitory, computer-readable medium according to claim 15, wherein the processor-executable instructions, when executed, further facilitate performance of the following:

determining, by the patient's mobile device, a location of the patient's mobile device; and transmitting, by the patient's mobile device, the determined location to a nurse station via the host device and the internal hospital network.

* * * * *